United States Patent [19]

Falinower

[11] 4,265,856

[45] May 5, 1981

[54] ANALYSIS REACTOR AND ITS USE FOR VOLUMETRIC ANALYSIS OF A SAMPLE OF A SUBSTANCE IN POWDER FORM

[75] Inventor: Charles Falinower, Montelimar, France

[73] Assignee: Ciments Lafarge France, Saint Cloud, France

[21] Appl. No.: 50,489

[22] Filed: Jun. 20, 1979

[30] Foreign Application Priority Data

Jun. 27, 1978 [FR] France .................. 78 19090

[51] Int. Cl.³ .......................................... G01N 27/28
[52] U.S. Cl. ...................................... 422/68; 422/76; 422/202; 422/203
[58] Field of Search ............... 422/68, 76, 102, 50, 422/150, 158, 130, 202, 203; 204/195 R, 195 T

[56] References Cited

U.S. PATENT DOCUMENTS

| | | | |
|---|---|---|---|
| 3,203,763 | 8/1965 | Kruse ............................ | 422/158 X |
| 3,787,481 | 1/1974 | Siclari et al. ..................... | 422/202 X |
| 3,870,465 | 3/1975 | Marechal ......................... | 23/230 A |
| 4,012,201 | 3/1977 | Powell et al. .................... | 422/158 X |

*Primary Examiner*—Ronald Serwin
*Attorney, Agent, or Firm*—Burgess, Ryan and Wayne

[57] ABSTRACT

This invention concerns an analysis reactor.

This reactor is characterized by the fact that it comprises a generally cylindrical body open at the bottom and surrounded by two annular chambers, an upper one containing an inlet pipe and opening into the reactor through a number of radial apertures and a lower one inside which a cooling agent circulates, the cylindrical body ending at the bottom in a base containing a drainage hole with a device to plug this hole. The reactor body also contains an overflow pipe below the upper chamber.

This invention also concerns the use of such a reactor to analyse a sample in powder form.

10 Claims, 3 Drawing Figures

ANALYSIS REACTOR AND ITS USE FOR VOLUMETRIC ANALYSIS OF A SAMPLE OF A SUBSTANCE IN POWDER FORM

This invention concerns an analysis reactor, and its use to analyse a sample of a substance in powder form, such as raw material for cement-making before it enters the clinker kiln.

This analysis naturally requires the sample for analysis to be weighed accurately. The French Pat. No. 78 19089 of June 27, 1978 describes a device to perform this accurate weighing and which is particularly suitable for connection to an analysis apparatus incorporating this new reactor, for the volumetric analysis of raw material for cement-making.

The invention provides for the combination of a weighing device and feed-mechanism for a sample of powder for analysis, such as raw material for cement-making, with an analysis apparatus consisting mainly of this new reactor.

This analysis apparatus is preferably designed to supply data which, in combination with data from the weighing device, are processed by a computer which indicates the relevant concentration of the raw material.

The invention consequently relates in particular to a reactor capable of receiving a sample of powder in suspension and designed so that its contents can be emptied automatically.

This new reactor is characterized by the fact that it comprises a generally cylindrical body open at the bottom and surrounded by two annular chambers, an upper one containing an inlet pipe, and opening into the reactor through a number of radial apertures, and a lower one inside which a cooling agent circulates, the bottom of this cylindrical body comprising a base containing a drainage hole, with a device to plug this hole, the body also containing an overflow outlet below the upper chamber.

According to one feature of the invention, this reactor is equipped with a measuring electrode and agitator system, which traverse a removable cover containing inlets to admit the sample for analysis and reagents.

Some of the upper chamber apertures lead in a radial direction towards the centreline of this chamber and are located on a common plane perpendicular to the centreline, while others lead in an oblique direction towards the chamber walls.

This invention also concerns a device to analyse a sample of a substance in powder form, such as raw material for cementmaking, combined with a weighing device and feed-mechanism for this sample, the said analysis device comprising an analysis reactor, means of storing and conveying reagents to this reactor, means of heating and agitating the contents of the reactor, means of feed-regulation and analysis of the contents, and means of emptying the reactor, which comprises a generally cylindrical body open at the bottom and surrounded by two annular chambers, one containing an inlet pipe, and opening into the reactor through a number of radial apertures, and a lower one, inside which a cooling agent circulates, the bottom of this cylindrical body comprising a base containing a drainage hole, with a device to plug this hole, the body also containing an overflow outlet below the upper chamber.

The reactor is preferably equipped with a measuring electrode and agitator, which traverse a removable cover containing inlets to admit the sample for analysis and reagents.

In another embodiment of the invention, the analysis device comprises a reactor heating system, round the base of the reactor, with a thermometer inside the reactor to monitor the temperature of the contents.

In one embodiment of this analysis device, the mechanism to plug the means of the reactor drainage hole consists of various systems such as a stopper fitted to the end of a swing-arm, to the other end of which a weight is attached, with a motor-driven cam which presses on this arm and raises the weight, separating the stopper from the seating against which the weight keeps it pressed. The plug system may also consist of a ball resting on a seat and operated by a vertical rod, movement of which is controlled by an electromagnet. The plug system may also consist of a moving piston fitted to the end of a motor-operated control rod, for covering or uncovering a drainage passage.

In another embodiment of this invention, the weighing device and feed-mechanism for the sample, and the system for storing and conveying reagents to the reactor, are the same as those described in the above French patent application No. 78 19089.

The following description, illustrated by the accompanying figures, will reveal other purposes and advantages of this invention which is however in no way confined to the embodiments described here.

Figure 1:
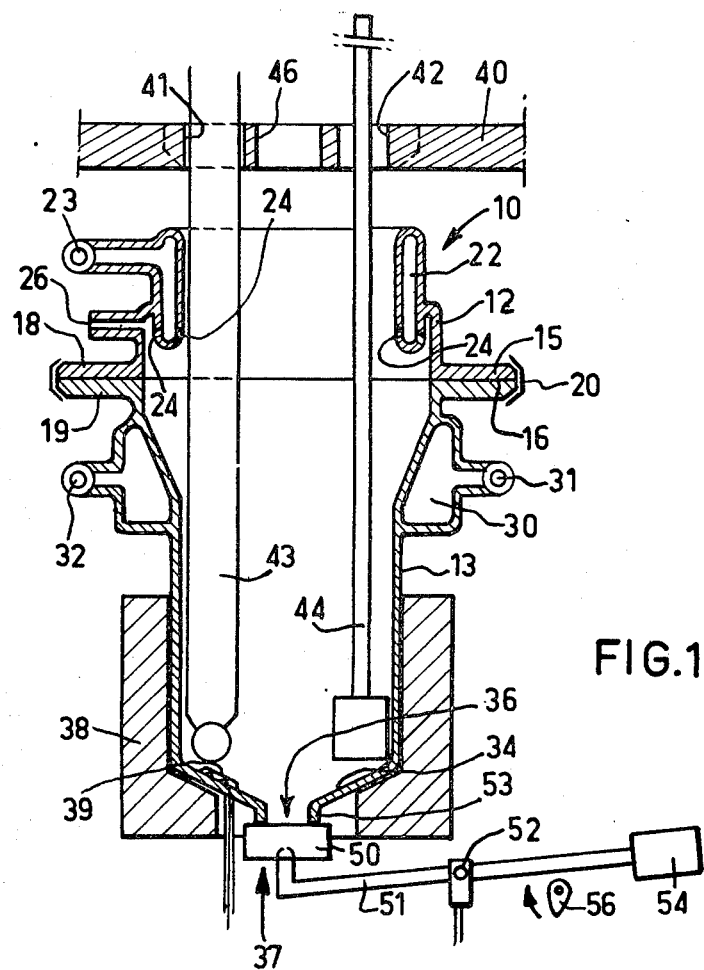
FIG. 1 is a cross-sectional view of one embodiment of the reactor, showing the system to plug the drainage hole.

FIG. 1 shows a glass reactor 10, generally cylindrical in form, open at the top and consisting here, for constructional reasons, of two parts, an upper part 12 and a lower part 13, connected together along two ground flat annular bearing surfaces 15 and 16 on the outside of flange 18 and 19 on the two parts 12 and 13. A ring 20, surrounding these flanges, holds the two parts of the reactor body togerther.

The upper part 12 contains an upper annular chamber 22, consisting of a space between the double walls of this part of the body, and with an inlet pipe 23. The bottom of this annular chamber contains a number of apertures 24 which lead radially in the direction of the chamber centreline, being located on a common plane perpendicular to this centreline and obliquely in relation to the walls. The wall of the upper part 12 contains an overflow pipe 26, located slightly above the plane of the apertures 24.

The lower part 13 contains a second annular chamber 30, just below the flange 19, with two passages 31 and 32 connected to a cooling agent source (not shown here).

This lower part 13 ends at the bottom in a generally conical base 34, containing a drainage hole 36 in the centre.

This drainage hole is equipped with a plug system 37, allowing it to be opened quickly to empty the reactor contents.

The base of the reactor, below the chamber 30, is surrounded by a heating system 38, which may be of any suitable type, for example with electrical heating resistances. A platinum thermocouple 39 fixed to the base of the reactor is used to monitor the temperature of the reaction mixture.

The top of the reactor is closed by lid 40, containing openings 41 and 42 through which the measuring electrode 43 and agitator arm 44 pass, and inlets 46 to admit the sample for analysis and various reagents.

In FIG. 1, the plug system 37 consists of a stopper 50 on the end of an arm 51 which pivots on a fixed axis 52, and is held hermetically against a sealing seating 53 round the edge of the hole 36 by the effect of a weight 54 attached to the other end of the arm 51.

A cam 56, operated by a motor (not shown here), presses on the arm 51 and raises the weight 54. When this happens, the stopper 50 moves away from the seating 53, and the reactor contents flow out through the hole 36.

Figures 2, 3:
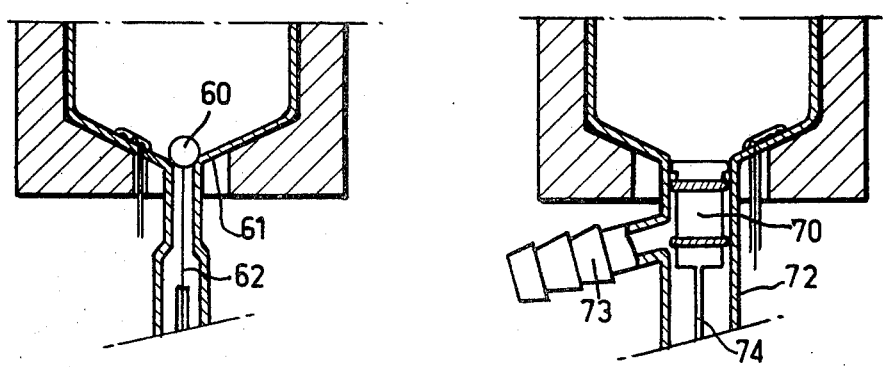
FIGS. 2 and 3 illustrate two embodiments of this plug system.

In FIG. 2, the plug system 37 consists of a ground spherical ball 60 which rests hermetically on a ground seating 61 round the edge of the hole 36 inside the reactor. This ball is connected to a vertical rod 62, operated by an electromagnet (not shown here). When this magnet is excited, it raises the rod, and the ball moves away from the seating 61.

In FIG. 3, the plug system consists of a sealing piston 7, moving inside a tube 72 surrounding the hole 36 and extending from the base of the reactor along the same centreline, with a side passage 73 leaving this tube in a radial direction. The piston 70 is fitted to the end of a driving rod 74, operated by a motor unit (not shown here). FIG. 3 shows the piston 70 in its upper position, covering the opening to the passage 73, and thus closing the reactor. When it moves down, it uncovers this opening, and the reactor contents flow out through the passage 73.

Other plug systems may be used with this reactor, provided that, as is the case for the methods described above, they provide a hermetic seal, despite the presence of an extremely abrasive reaction mixture, containing solids in suspension.

The actual analysis operation takes place as follows.

A given quantity of distilled water, e.g. 20 cc, is admitted into the reactor through the inlet pipe 23, chamber 22 and apertures 24. The heating system 36, regulated by means of the thermocouple 39, is started up.

The sample for analysis is then admitted, for example by using the weighing device described in the patent application already referred to. An excess quantity of hydrochloric acid, such as 20 cc. 2.5 N acid, is then admitted into the reactor, and a further quantity of distilled water, for example 20 cc, is again admitted through inlet pipe 23, and the mixture is stirred by means of the agitator 44.

Admission of this second quantity of distilled water, entering the reactor through apertures 24, washes the wall of the reactor and the instruments inside, and carries away any particles adhering to this wall.

The acid is left to attack the sample for 3 to 4 minutes, after which the heating is turned off and actual analysis carried out, using a basic solution of known strength, such as 1.1 N NaOH, the electrode 43 being used to measure the pH-value.

The deleterious vapour released during the reaction condenses on the wall of the chamber 30, under the effect of the cooling agent.

Since the exact weight of sample is known, its strength can be determined by measuring the quantity of basic solution needed to neutralize the excess acid; this is known by means of an electronic burette connected to a titrator with a preset final point, for example using the computer in the device described in the patent application already referred to.

When measurement is completed, the reactor is drained by opening the drainage hole 36, and the reactor is rinsed out using the upper chamber 22 to admit a suitable liquid.

In a recommended embodiment of the invention, the reactor and its accessories and analysis appliances, as well as stored reagents, are installed in a single unit.

This unit is preferably combined with the titration device described in the French Patent Application already referred to.

Naturally, this invention is in no way confined to the embodiments described and illustrated here: many variants are available for someone skilled in the art, depending on what application is involved and without any departure from the spirit of the invention.

What is claimed is:

1. A reactor for analyzing a powder substance mixed with a liquid, comprising a substantially cylindrical upright body having an open upper end adapted for introducing the powder sample into said body, a sealable bottom end opening, means for heating a lower portion of said cylindrical body adjacent the bottom end thereof, sealing means for sealing and opening said bottom end opening, liquid inlet means for introducing a liquid into said cylindrical body in a circumferential inlet area adjacent to said top end of said body, said liquid inlet means adapted to direct at least a portion of said liquid toward the inner wall surface of said cylindrical body in an annular zone adjacent to said circumferential liquid inlet area, means for cooling the inner wall of said body in a circumferential zone located beneath, and comparatively close to, said circumferential inlet area, stirring means arranged within said cylindrical body near the bottom thereof and analyzing electrode means adapted to be immersed in the mixture of said sample and said liquid within said body.

2. A reactor according to claim 1, wherein said liquid inlet means comprises an upper circumferential chamber surrounding an upper portion of said cylindrical body adjacent the top end thereof and provided with liquid inlet conduit means for introducing said liquid into said upper chamber, said upper chamber having circumferentially distributed passages provided at the lower end of said upper chamber for allowing said liquid introduced into said upper chamber to flow into the inner space of said cylindrical body.

3. A reactor according to claim 1 or 2, wherein said cooling means comprises a lower circumferential chamber coaxial to said upper chamber and located at a distance below the upper chamber, said lower chamber having a cooling fluid inlet and a cooling fluid outlet allowing a cooling liquid to be circulated through said lower chamber, said cooled circumferential cylindrical body inner wall zone beng constituted by a wall portion of said lower chamber, which is directed inwardly with respect to said cylindrical body.

4. A reactor according to claim 3, wherein said inwardly directed wall portion of said lower chamber presents an inwardly and downwardly tapering shape.

5. A reactor according to claim 1 or 2, wherein the lowermost end portion of said cylindrical body is tapered inwardly and downwardly and is provided with electrical means for measuring and monitoring the temperature of the contents of said body.

6. A reactor according to claim 1, wherein said bottom end opening sealing means comprises a sealing member mounted on one end of a swing-arm adapted to be pressed against the circumferential edge of said bottom end opening under the effect of a counter-weight, a motor-driven cam being provided for acting on said swing-arm so as to move the same into a position wherein it disengages said sealing member from said bottom end opening.

7. A reactor according to claim 1, wherein said bottom end opening sealing means comprises a ball adapted to rest on a seating surface surrounding said bottom end opening inside said cylindrical body, and a vertically movable rod in communication with said ball arranged to disengage said ball from said seating surface.

8. The reactor of claim 7 wherein said movable rod is actuated by an electromagnet.

9. A reactor according to claim 1, wherein said bottom end opening sealing means comprises a sealing piston axially movable in a tube extending downwardly from said bottom end opening, said tube having a lateral outlet aperture arranged to be selectively sealed or cleared by said piston, the axial movement of said piston being controlled by a control rod actuated by a motor.

10. A reactor according to claim 1, wherein an overflow is provided in said cylindrical body at a level slightly above the level of said liquid inlet area.

* * * * *